US012303447B2

(12) United States Patent
Sanz et al.

(10) Patent No.: US 12,303,447 B2
(45) Date of Patent: May 20, 2025

(54) TELEKINETIC BIONIC GLOVE ASSEMBLY

(71) Applicant: Animo Bionics Corp., Miami, FL (US)

(72) Inventors: Ian D. Sanz, Miami, FL (US); Harold Magdalena, Miami, FL (US)

(73) Assignee: Animo Bionics Corp.

( * ) Notice: Subject to any disclaimer, the term of this patent is extended or adjusted under 35 U.S.C. 154(b) by 760 days.

(21) Appl. No.: 17/579,234

(22) Filed: Jan. 19, 2022

(65) Prior Publication Data

US 2023/0225924 A1    Jul. 20, 2023

(51) Int. Cl.
*A61H 1/02*    (2006.01)
(52) U.S. Cl.
CPC ...  *A61H 1/0288* (2013.01); *A61H 2201/1215* (2013.01); *A61H 2201/149* (2013.01); *A61H 2201/1635* (2013.01); *A61H 2201/165* (2013.01); *A61H 2201/5007* (2013.01); *A61H 2201/5025* (2013.01)
(58) Field of Classification Search
CPC .. A61H 1/0218; A61H 1/0285; A61H 1/0288; A61H 2201/1215; A61H 2201/149; A61H 2201/1635; A61H 2201/165; B25J 9/0006
See application file for complete search history.

(56) References Cited

U.S. PATENT DOCUMENTS

| 2005/0119833 | A1* | 6/2005 | Nanikashvili | G16H 40/67 |
| | | | | 702/19 |
| 2006/0167564 | A1* | 7/2006 | Flaherty | A61B 5/11 |
| | | | | 623/57 |
| 2010/0041521 | A1* | 2/2010 | Ingvast | B25J 9/0006 |
| | | | | 482/49 |
| 2019/0091091 | A1 | 3/2019 | Park et al. | |
| 2020/0281797 | A1* | 9/2020 | Yang | A61H 1/0218 |
| 2022/0023133 | A1* | 1/2022 | Woge | A61B 5/225 |
| 2022/0040027 | A1* | 2/2022 | Catarino Palomo | |
| | | | | A61H 1/0288 |

FOREIGN PATENT DOCUMENTS

WO    WO-2017072463 A1 *  5/2017   ........... A61H 1/0288

OTHER PUBLICATIONS

WO2017072463A1 machine translation accessed Dec. 11, 2024 (Year: 2024).*

* cited by examiner

*Primary Examiner* — Victoria Murphy
*Assistant Examiner* — Kelsey Rhee
(74) *Attorney, Agent, or Firm* — ALBERT BORDAS P.A.

(57) ABSTRACT

A telekinetic bionic glove assembly having a glove assembly, first and second boxes attached to the glove assembly, an arm box, and an electrical lead assembly connected to the arm box. The glove assembly has string guides positioned on glove fingers. The glove assembly also has a main bar and bands positioned at a glove back face, and a thumb splint. The first box has strings, motors, a motor controller, and reels. The second box has a voltage regulator, a battery, and a computer. The arm box has an arm box computer, an arm box voltage regulator, a bio-signal amplifier, an arm box battery, and arm box switch. The electrical lead assembly has electrical leads, lead heads, electrodes, and adhesive pads. The glove assembly operates, whereby the glove fingers open and close in response to voltage spikes as results of eye movements.

19 Claims, 6 Drawing Sheets

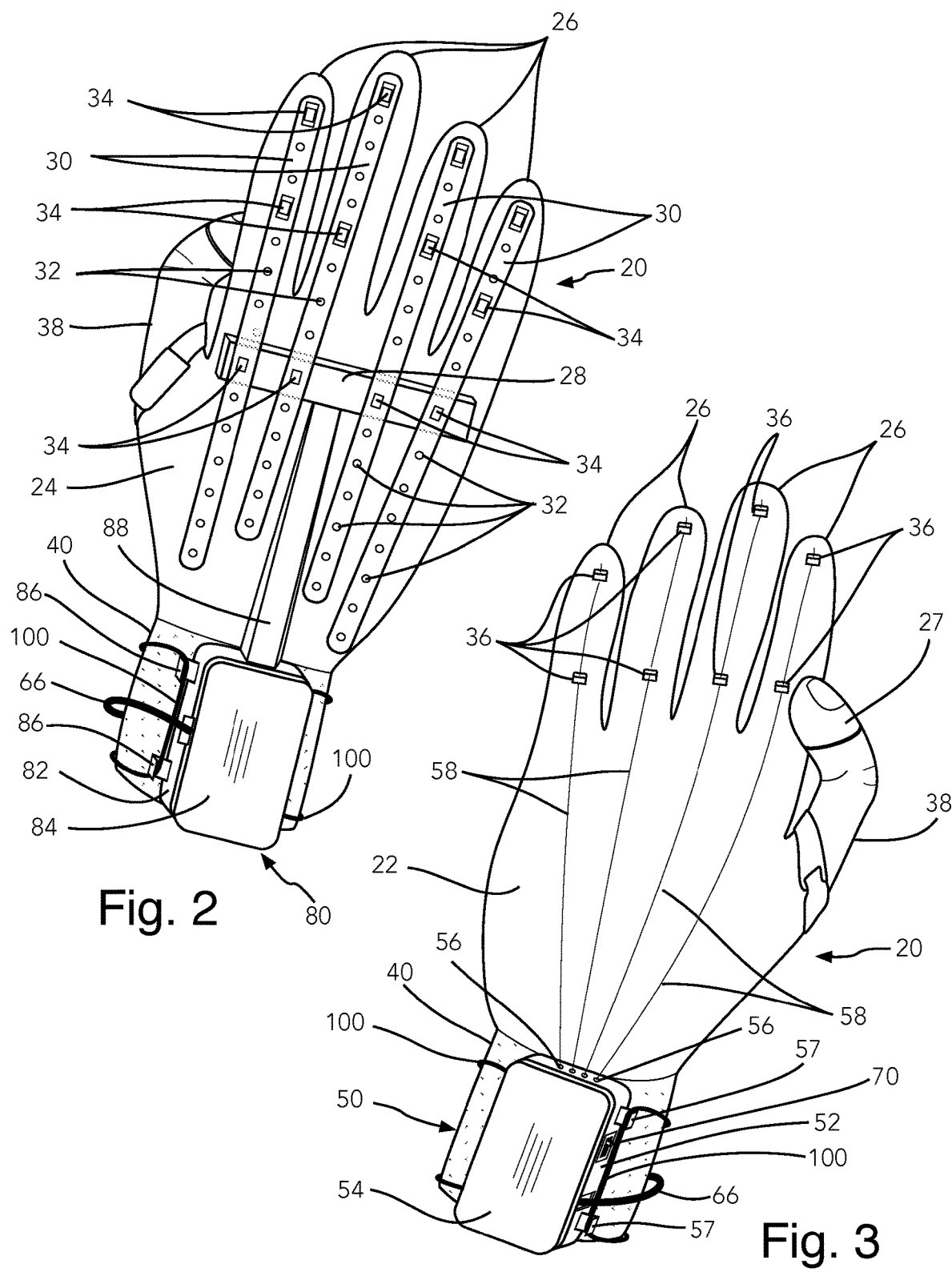

TELEKINETIC BIONIC GLOVE ASSEMBLY

BACKGROUND OF THE INVENTION

1. Field of the Invention

The present invention relates to bionic devices, and more particularly, to bionic gloves.

2. Description of the Related Art

Applicant believes that one of the closest references corresponds to U.S. Patent Application Publication No. US 2019/0091091 A1, published on Mar. 28, 2019 to Park, et al. for an apparatus for assisting in finger motion. However, it differs from the present invention because Park, et al. teach a finger-motion assisting apparatus comprising a wearing part, a first cover extending from the wearing part to one side, first and second wires pulling the first cover, a pulley around which the first and second wires are wound, and a motor rotating the pulley. The first and second wires are arranged from a first point to a second point of the first cover along the extension direction of the first cover and arranged along at least part of a periphery of the first cover in opposite directions at the second point of the first cover.

Other patents describing the closest subject matter provide for a number of more or less complicated features that fail to solve the problem in an efficient and economical way. None of these patents suggest the novel features of the present invention.

SUMMARY OF THE INVENTION

The present invention is a telekinetic bionic glove assembly, comprising a glove assembly, a first box, a second box, an arm box; and an electrical lead assembly, wherein the first and second boxes are attached to the glove assembly, and the electrical lead assembly is connected to the arm box.

The glove assembly comprises string guides positioned on glove fingers at a glove palm face. The glove assembly further comprises a main bar and bands at a glove back face, and the glove assembly further comprises a thumb splint on thumb. The string guides are attached to an index finger, a middle finger, a ring finger, and a little finger. The main bar is horizontally oriented at the glove back face and the bands are mounted onto the main bar and attached to the glove fingers, whereby a first band is attached to the index finger, a second band is attached to the middle finger, a third band is attached to the ring finger, and a fourth band is attached to the little finger.

The first box is attached to a forearm section of the glove assembly at the glove palm face, and connects to the second box attached to the forearm section of the glove assembly at the glove back face. The first box comprises a case having a cover, case holes, a switch, a first lateral protrusion having a first set of holes and a second lateral protrusion having a second set of holes. The first box further comprises strings, first and second motors, a motor controller, and first and second reels.

The strings extend from the glove fingers to the first and second reels, whereby the index finger and the middle finger share a first string, which is threaded through and wound upon the first reel and the ring finger, and the little finger share a second string, which is threaded through and wound upon the second reel. The string guides secure the strings to the glove fingers. The first and second motors are connected to the first and second reels respectively.

The second box comprises a case having a cover, a main bar connector, a voltage regulator, a battery, and a computer. The main bar connector connects perpendicularly to the main bar, whereby the main bar connector connected to the main bar are T-shaped.

The arm box comprises an arm box case having an arm box cover, an arm box computer, an arm box voltage regulator, a bio-signal amplifier, an arm box battery, and an arm box switch.

The electrical lead assembly comprises first and second electrical leads, first and second lead heads, first and second electrodes, and first and second adhesive pads. The glove assembly is adapted to be used on a hand and eyes of a subject in need of the telekinetic bionic glove assembly, whereby the glove fingers open and close in response to a predetermined closing of the eyes that generates a voltage spike for a predetermined time. The arm box is adapted to be worn on an arm, whereby the arm box is worn opposite to the hand wearing the glove assembly.

The first electrical lead having the first lead head is adapted to be worn behind a mastoid bone of an outer ear, and the second electrical lead having the second lead head is adapted to be worn at a temple area or above a respective eye. The second electrical lead connected to the second electrode reads voltage after a first voltage spike that is processed by the arm box computer, and a computer of the second box receives a signal via a short-range wireless technology standard to operate the first and second motors to activate the first and second reels, whereby the first and second reels wind up respective the strings causing the glove fingers to move towards the glove palm face to close a predetermined amount. A second voltage spike activates the first and second motors, whereby the first and second reels wind down respective the strings, while respective bands exert a predetermined force onto the glove fingers to return to an open position. The first and second motors are activated when the voltage spike for between 1 and 2 seconds.

It is therefore one of the main objects of the present invention to provide a telekinetic bionic glove assembly.

It is another object of this invention to provide a telekinetic bionic glove assembly to be used by a subject in need of such glove assembly to move a hand.

It is another object of this invention to provide a telekinetic bionic glove assembly to be used by a subject in need of such glove assembly to move fingers and hold an object.

It is another object of this invention to provide a telekinetic bionic glove assembly by which the subject in need of such glove can close fingers of a hand when the subject closes their eyes for a predetermined time.

It is another object of this invention to provide a telekinetic bionic glove assembly, which has electrodes to register ocular movement signals.

It is another object of this invention to provide a telekinetic bionic glove assembly that is volumetrically efficient for carrying, transporting, and storage.

It is another object of this invention to provide a telekinetic bionic glove assembly, which is of a durable and reliable construction.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combi

FIG. 2 is a top isometric view of a glove assembly of the present invention.

FIG. 3 is a bottom isometric view of the glove assembly of the present invention.

DETAILED DESCRIPTION OF THE PREFERRED EMBODIMENT

Figure 1:
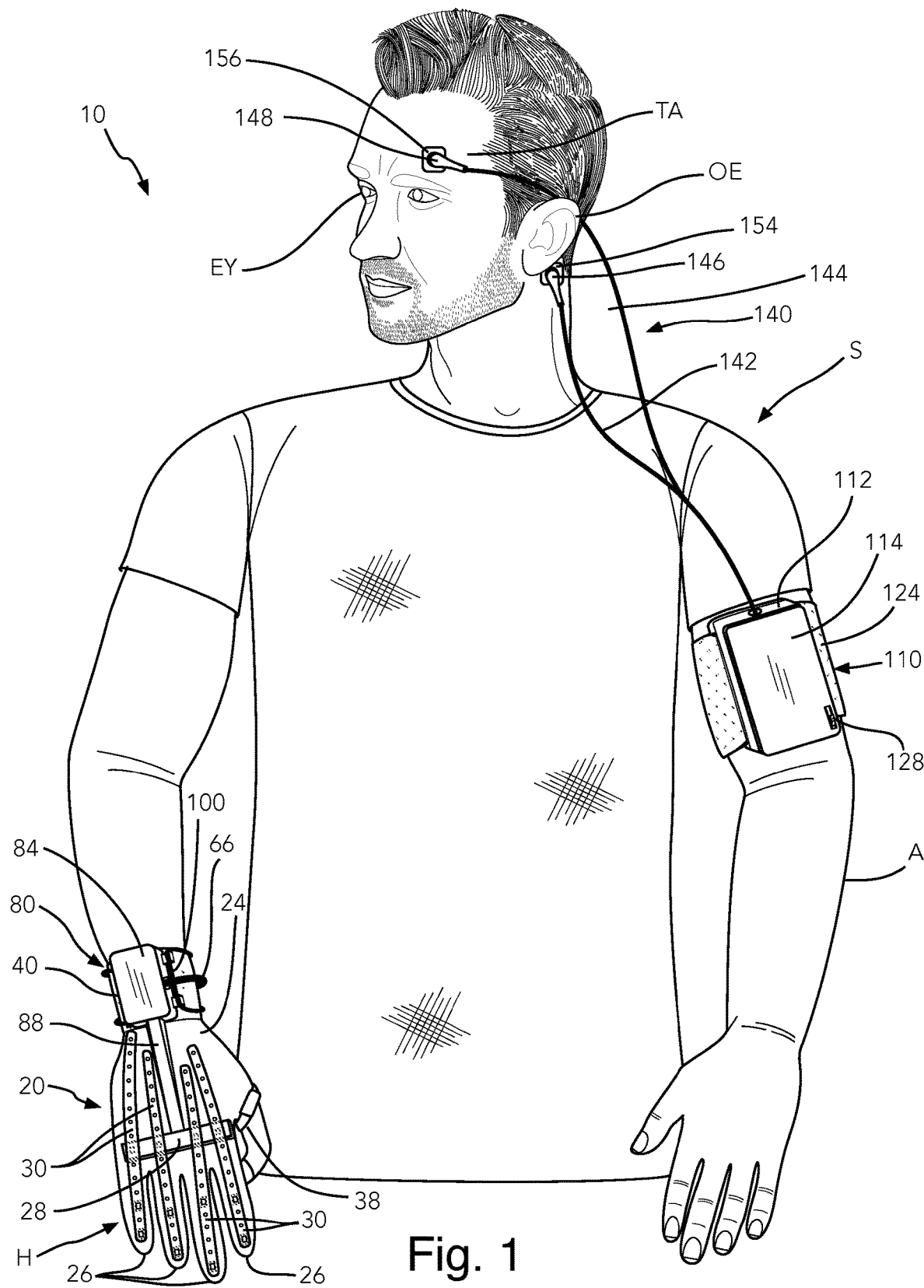
- FIG. 1 is a representation of the present invention as worn by a user defined as a subject.

Referring now to the drawings, the present invention is a telekinetic bionic glove assembly, and is generally referred to with numeral 10. It can be observed that it basically includes glove assembly 20, first box 50, second box 80, arm box 110, and electrical lead assembly 140.

As seen in FIG. 1, present invention 10 is adapted to be worn by a subject S in need thereof. Subject S may be someone that suffers from partial or full paralysis, someone that is overcoming an injury or rehabilitating, or otherwise anyone that does not have sufficient hand/finger strength to open and close a particular hand. Glove assembly 20 is worn on such a hand H of subject S, whereby glove fingers 26 move in response to a predetermined closing of eyes EY that generates a voltage spike for a predetermined time. In a preferred embodiment, the spike in voltage occurs when subject S keeps their eyes EY closed between 1 and 2 seconds.

Second box 80 is attached to forearm section 40 of glove assembly 20 at glove back face 24. Arm box 110 is worn on an arm A that is opposite to hand H wearing glove assembly 20. Arm box 110 comprises arm band 124 to secure arm box 110 to arm A.

Electrical lead assembly 140 connects to arm box 110. First electrical lead 142, having lead head 146, is positioned behind a mastoid bone of outer ear OE. Second electrical lead 144, having lead head 148, is positioned at temple area TA or above a respective eye EY. It is noted that the mastoid bone of outer ear OE, and the respective eye EY are also opposite to hand H wearing glove assembly 20. Therefore, first electrical lead 142 and second electrical lead 144 are positioned at a same side of arm box 110.

As seen in FIGS. 2 and 3, glove assembly 20 comprises glove palm face 22, glove back face 24, glove fingers 26, and thumb 27. Glove back face 24 comprises main bar 28 and bands 30. In a preferred embodiment, bands 30 are four semirigid silicone bands. Main bar 28 is horizontally oriented and attached at glove back face 24 and bands 30 are mounted onto main bar 28 and attached to glove fingers 26, whereby a first band 30 is attached to an index finger, a second band 30 is attached to a middle finger, a third band 30 is attached to a ring finger, and a fourth band 30 is attached to a little finger. In a preferred embodiment, bands 30 comprise band holes 32. Glove fingers 26 comprise protrusions 34, whereby each hole 32 receives one protrusion 34 to secure each band 30 onto glove back face 24 of glove assembly 20.

Thumb 27 comprises thumb splint 38, so that thumb 27 remains in a slightly bent position. First box 50 and second box 80 are attached to glove assembly 20. First box 50 comprises tabs 57 and second box 80 comprises tabs 86. Tabs 57 and 86 receive side bands 100 at each side of boxes 50 and 80 to avoid first and second boxes 50 and 80 from moving around the wrist during tensioning. First box 50 and second box 80 are connected with wires 66.

Second box 80 comprises main bar connector 88 that connects perpendicularly to main bar 28, whereby main bar connector 88 connected to main bar 28 are T-shaped.

Figure 4:
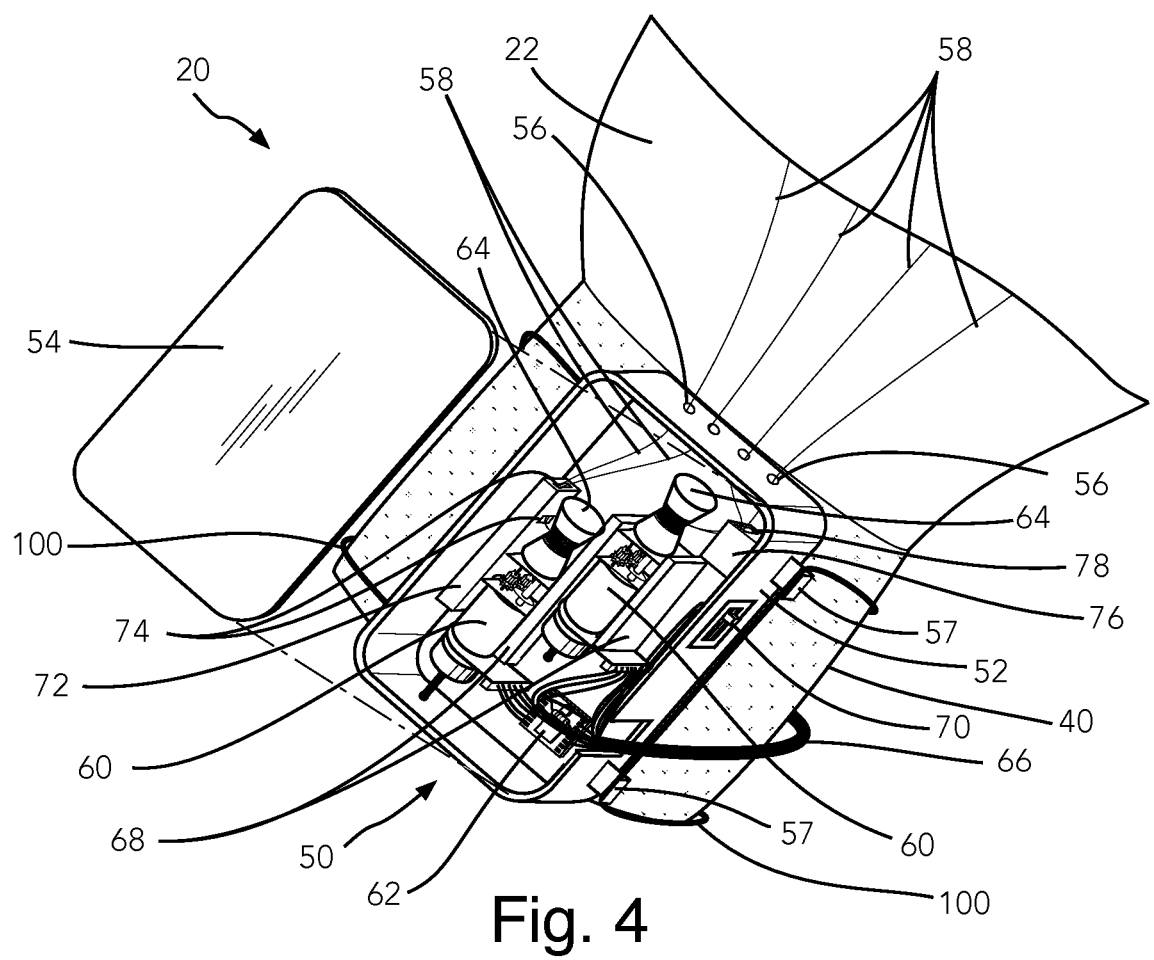
FIG. 4 is an isometric view of a first box of the present invention showing respective parts inside.

As seen in FIGS. 3 and 4, glove fingers 26 comprise string guides 36 positioned at glove palm face 22. String guides 36 secure strings 58 to glove fingers 26.

In a preferred embodiment, first box 50 comprises first and second strings 58. The index and middle fingers share a first string 58, which is threaded through and wound upon a first reel 64. Distal ends of the first string 58 pass through a first set of holes 74 on lateral protrusion 72, are separated to pass through respective case holes 56, and are secured along the index and middle fingers respectively.

The ring and little fingers share a second string 58, which is threaded through and wound upon a second reel 64. Distal ends of the second string 58 pass through a second set of holes 78 on lateral protrusion 76, are separated to pass through respective case holes 56, and are secured along the ring and little fingers respectively.

As seen in FIG. 4, first box 50 is attached to forearm section 40 of glove assembly 20 at glove palm face 22. First box 50 comprises case 52 having cover 54, case holes 56, internal walls 68, and switch 70. First box 50 further comprises strings 58, first and second motors 60, motor controller 62, and first and second reels 64. First and second motors 60 connect to first and second reels 64 respectively. Strings 58 extend from glove fingers 26 to first and second reels 64. In a preferred embodiment, strings 58 pass through case holes 56 and wind upon respective reels 64.

Figure 4A:
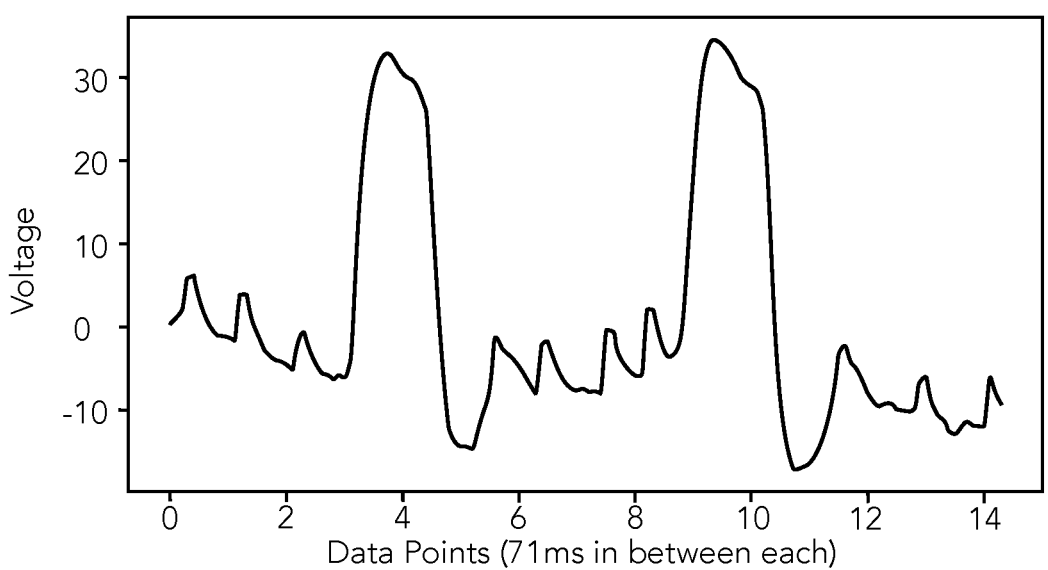
FIG. 4A is a graphic representing electrooculographic control of the present invention.

As seen in FIGS. 4 and 4A, in operation, closing of eyes EY, seen in FIG. 1, generates a voltage spike for a predetermined time to activate first and second motors 60. Activated first and second motors 60 open/close glove assembly 20 when a voltage exceeds a given threshold for a given duration. In a preferred embodiment, first and second motors 60 are activated when the voltage spike for between 1 and 2 seconds, whereby subject S keeps their eyes EY closed between the 1 and 2 seconds. In a preferred embodiment, the voltage is between 15 and 25 centivolts. In another preferred embodiment, first and second motors 60 are activated when the voltage is at least 20 centivolts for between 1 and 2 seconds.

Figure 5:
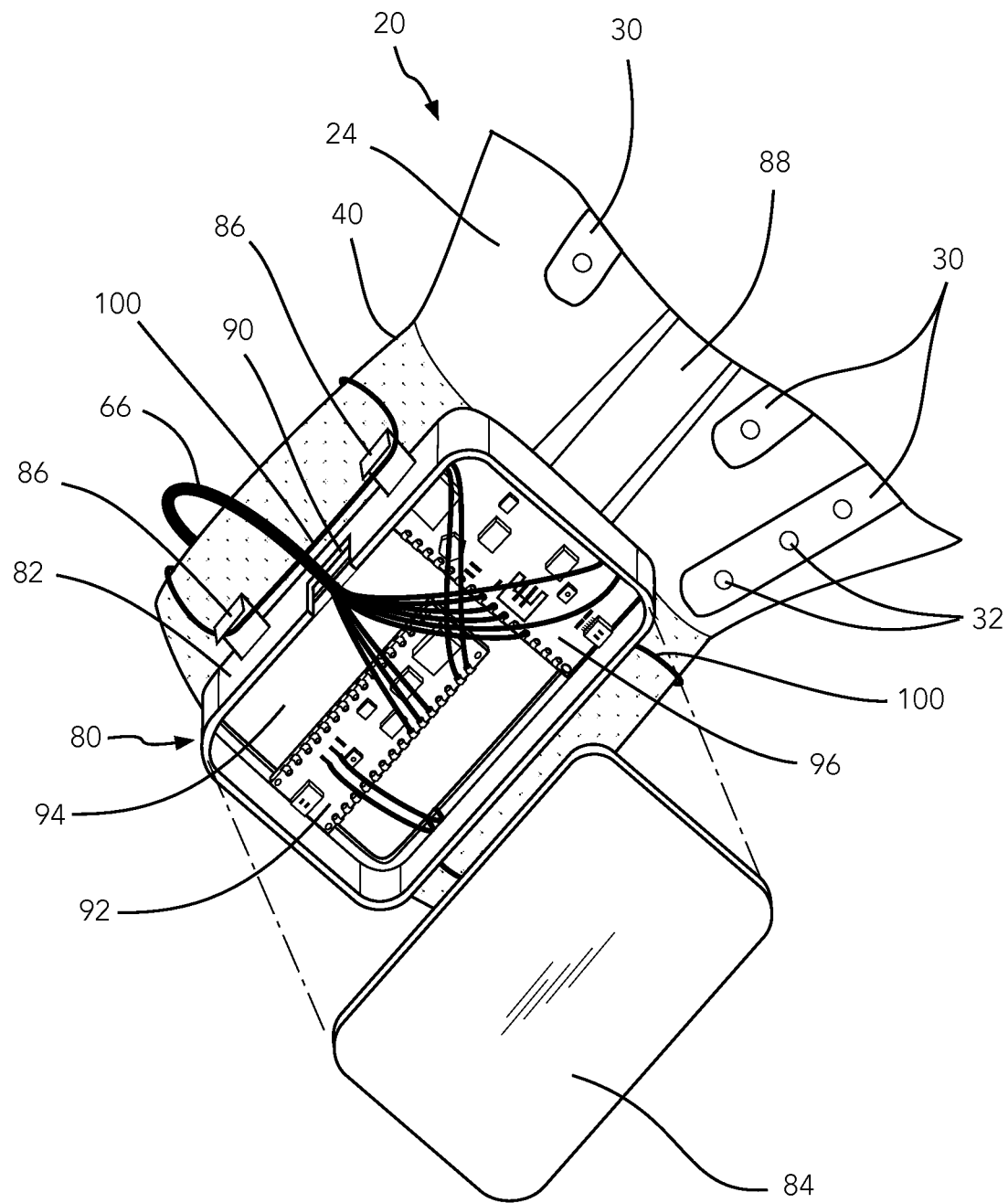
FIG. 5 is an isometric view of a second box of the present invention showing respective parts inside.

As seen in FIG. 5, second box 80 comprises case 82 having cover 84, main bar connector 88, voltage regulator 92, battery 94, and computer 96. Second box 80 further comprises indent 90 by which wires 66 pass through to connect to first box 50, seen in FIG. 4.

Figure 6:
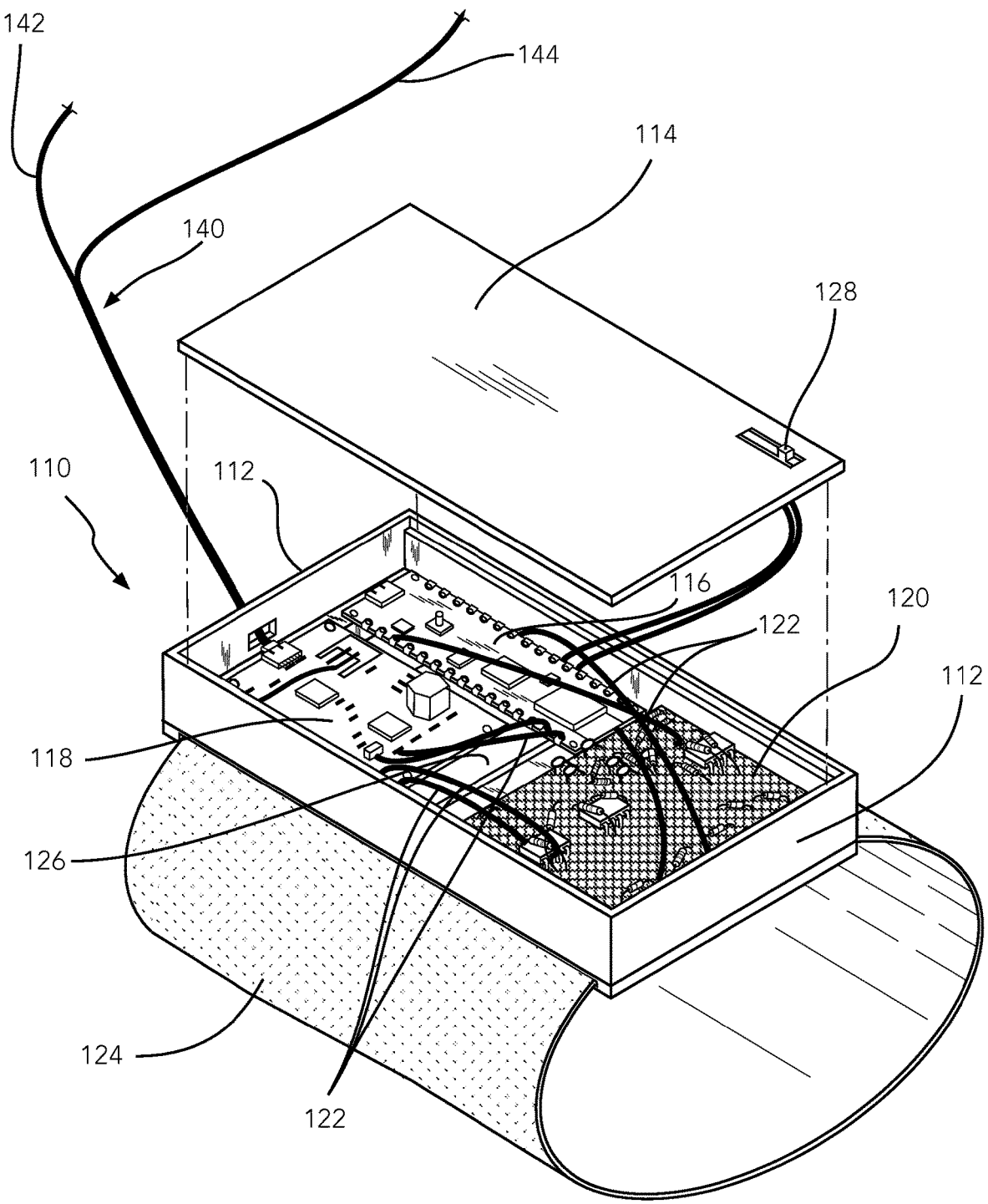
FIG. 6 is an isometric view of an arm box of the present invention showing respective parts inside.
Figure 7A:
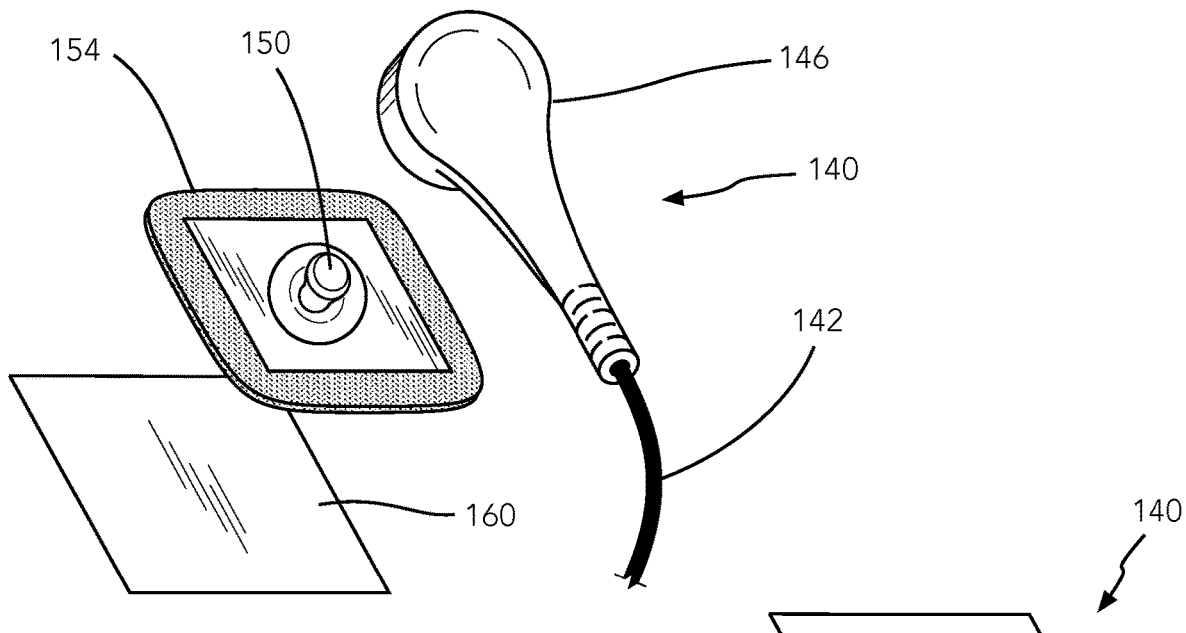
FIG. 7A is an isometric view of an electrical lead assembly with a first electrical lead.

As seen in FIGS. 5 and 6, second electrical lead 144, connected to second electrode 152, seen in FIG. 7A, reads a voltage, which is processed by arm box computer 116, and computer 96 of second box 80, receives a signal via a short-range wireless technology standard to operate first and second motors 60 seen in FIG. 4. As further seen in FIG. 4, first and second motors 60 activate first and second reels 64, whereby first and second reels 64 wind up respective strings 58 causing glove fingers 26 to move towards glove palm face 22 to close hand H, seen in FIG. 1, a predetermined amount so as to grip an object, not seen. It is noted that first and second motors 60 have sufficient power to overcome a predetermined force of bands 30. When subject S wants to open hand H, closing of eyes EY for a predetermined time again generates another voltage spike to again activate first and second motors 60, whereby first and second reels 64 wind down respective strings 58, seen in FIG. 4, while respective bands 30 exert the predetermined force onto glove fingers 26 to return to an open position, seen in FIG. 1.

As seen in FIG. 6, arm box 110 comprises arm box case 112 having arm box cover 114, arm box computer 116, arm box voltage regulator 118, and bio-signal amplifier 120, arm box battery 126, and arm box switch 128. Arm box 110 further comprises internal wires 122. Electrical lead assembly 140 is connected to arm box 110.

Figure 7B:
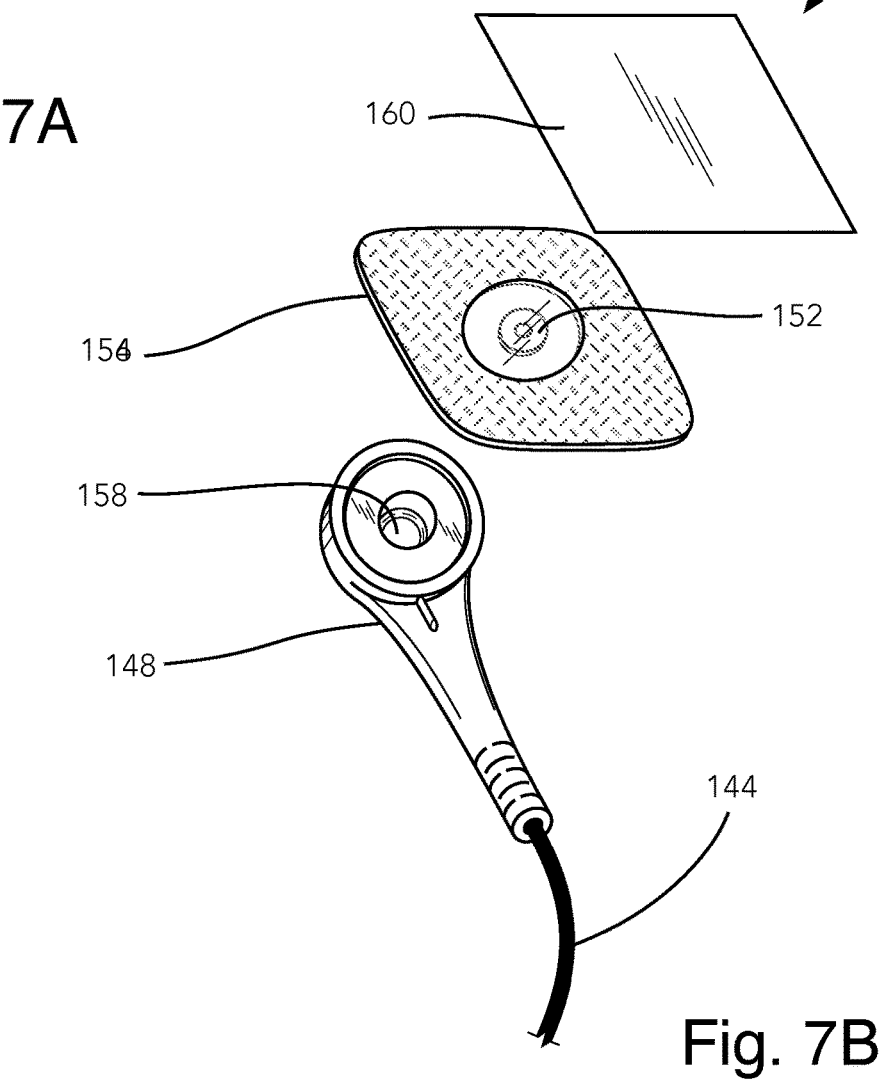
FIG. 7B is an isometric view of the electrical lead assembly with a second electrical lead.

As seen in FIGS. 7A and 7B, electrical lead assembly 140 comprises first and second electrical leads 142 and 144, respective first and second lead heads 146 and 148, respective first and second electrodes 150 and 152, and respective first and second adhesive pads 154 and 156 each having a cover 160.

In use, first adhesive pad 154 having first electrode 150 thereon, sticks behind the mastoid bone of outer ear OE, and second adhesive pad 156 having second electrode 152 thereon, sticks at temple area TA or above respective eye EY as seen in FIG. 1. First and second lead heads 146 and 148 are connected to respective first and second electrodes 150 and 152, whereby first and second lead heads 146 and 148 each comprise a hole 158 to receive respective electrodes 150 and 152. First electrical lead 142, connected to first electrode 150 is for grounding, and second electrical lead 144 connected to second electrode 152 is for reading a voltage.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A telekinetic bionic glove assembly, comprising:
    A) a glove assembly;
    B) a first box, comprising a case having a cover, case holes, a switch, a first lateral protrusion having a first set of holes and a second lateral protrusion having a second set of holes;
    C) a second box;
    D) an arm box; and
    E) an electrical lead assembly, wherein said first and second boxes are attached to said glove assembly, and said electrical lead assembly is connected to said arm box.

2. The telekinetic bionic glove assembly set forth in claim 1, wherein said glove assembly comprises string guides positioned on glove fingers at a glove palm face, said glove assembly further comprises a main bar and bands at a glove back face, and said glove assembly further comprises a thumb splint on thumb.

3. The telekinetic bionic glove assembly set forth in claim 2, wherein said string guides are attached to an index finger, a middle finger, a ring finger, and a little finger.

4. The telekinetic bionic glove assembly set forth in claim 3, wherein said main bar is horizontally oriented at said glove back face and said bands are mounted onto said main bar and attached to said glove fingers, whereby a first band is attached to said index finger, a second band is attached to said middle finger, a third band is attached to said ring finger, and a fourth band is attached to said little finger.

5. The telekinetic bionic glove assembly set forth in claim 2, wherein said first box is attached to a forearm section of said glove assembly at said glove palm face, connecting to said second box attached to said forearm section of said glove assembly at said glove back face.

6. The telekinetic bionic glove assembly set forth in claim 3, wherein said first box further comprises strings, first and second motors, a motor controller, and first and second reels.

7. The telekinetic bionic glove assembly set forth in claim 6, wherein said strings extend from said glove fingers to said first and second reels, whereby said index finger and said middle finger share a first string, which is threaded through and wound upon said first reel and said ring finger and said little finger share a second string, which is threaded through and wound upon said second reel.

8. The telekinetic bionic glove assembly set forth in claim 6, wherein said string guides secure said strings to said glove fingers.

9. The telekinetic bionic glove assembly set forth in claim 6, wherein said first and second motors are connected to said first and second reels respectively.

10. The telekinetic bionic glove assembly set forth in claim 6, wherein said second box comprises a case having a cover, a main bar connector, a voltage regulator, a battery, and a computer.

11. The telekinetic bionic glove assembly set forth in claim 10, wherein said main bar connector connects perpendicularly to said main bar, whereby said main bar connector connected to said main bar are T-shaped.

12. The telekinetic bionic glove assembly set forth in claim 1, wherein said arm box comprises an arm box case having an arm box cover, an arm box computer, an arm box voltage regulator, an arm box battery, an arm box switch, and a bio-signal amplifier.

13. The telekinetic bionic glove assembly set forth in claim 10, wherein said electrical lead assembly comprises first and second electrical leads, first and second lead heads, first and second electrodes, and first and second adhesive pads.

14. The telekinetic bionic glove assembly set forth in claim 13, wherein said glove assembly is adapted to be used on a hand and eyes of a subject in need of said telekinetic bionic glove assembly, whereby said glove fingers open and close in response to a predetermined closing of said eyes that generate a voltage spike for a predetermined time.

15. The telekinetic bionic glove assembly set forth in claim 1, wherein said arm box is adapted to be worn on an arm, whereby said arm box is worn opposite to said hand wearing said glove assembly.

16. The telekinetic bionic glove assembly set forth in claim 14, wherein said first electrical lead having said first lead head is adapted to be worn behind a mastoid bone of an outer ear, and said second electrical lead having said second lead head is adapted to be worn at a temple area or above a respective of said eyes.

17. The telekinetic bionic glove assembly set forth in claim 14, wherein said second electrical lead connected to said second electrode reads voltage after a first voltage spike that is processed by said arm box computer, and a computer of said second box receives a signal via a short-range wireless technology standard to operate said first and second motors to activate said first and second reels, whereby said first and second reels wind up respective said strings causing said glove fingers to move towards said glove palm face to close a predetermined amount.

18. The telekinetic bionic glove assembly set forth in claim 17, wherein a second voltage spike activates said first and second motors, whereby said first and second reels wind down respective said strings, while respective said bands exert a predetermined force onto said glove fingers to return to an open position.

19. The telekinetic bionic glove assembly set forth in claim 17, wherein said first and second motors are activated when said voltage spike for between about 1 and 2 seconds.

\* \* \* \* \*